Feb. 19, 1935. R. KAUCHER Plant Pat. 121
ROSE
Filed July 18, 1934
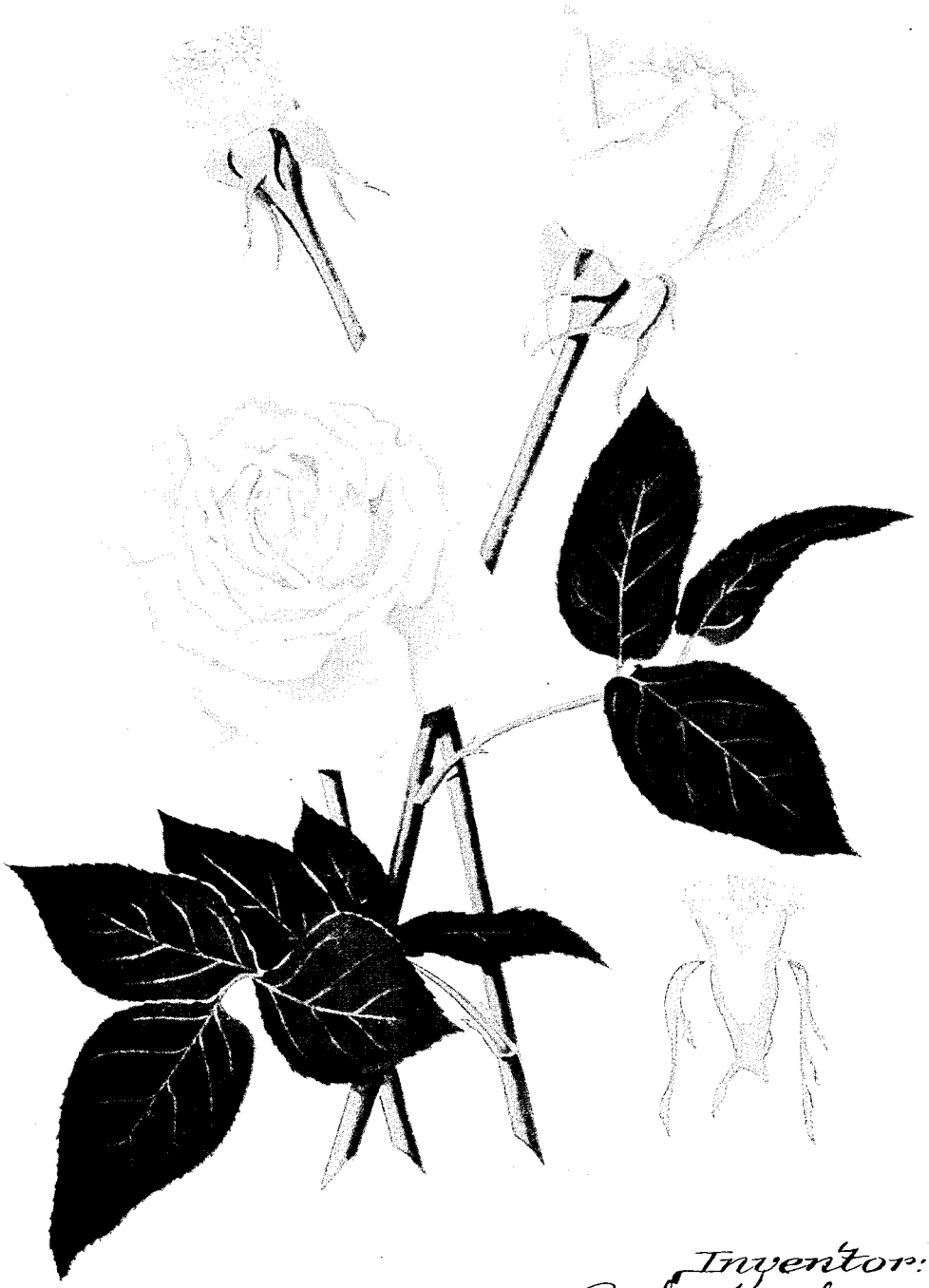
Inventor:
Ruth Kaucher
By Orville M. Kile
Plant patent agent Patented Feb. 19, 1935

Plant Pat. 121

UNITED STATES PATENT OFFICE

121

ROSE

Ruth Kaucher, Newtown, Pa.

Application July 18, 1934, Serial No. 735,864

1 Claim. (Cl. 47—61)

My present invention relates to improvements in fragrant hybrid tea roses predominantly white in color but with flesh pink central petals. My new variety is a sport of the variety known as Premiere Supreme. It was discovered and developed by myself. In addition to its distinctive coloring this new variety is notable particularly for its vigorous growth, free blooming, very large flowers having forty to fifty petals, and its long-lasting qualities, and is especially unique in the peculiar cone-shaped, raised center to which the petals are attached at the base of the blossom.

The accompanying illustrations show in full color a partly opened bud; a blossom well opened; the cone-shaped, raised center remaining after the petals are plucked off; and (at the right) a vertical section view of this cone-shaped body.

The following is a detailed description of the plant, flower and other features;

*Plant.*—Vigorous in growth, about 5 feet tall, very resistant to mildew and leaf spot, does not produce blind wood, and usually bears 25 to 30 blossoms per plant in a season.

*Stems.*—Forest green in color, (Ridgway's Color Standards and Nomenclature, Plate XVII) rather stout, inclined to the zig-zag form rather than straight, entirely free of thorns and spines for the first ten inches to one foot below the flower. Hips moderately thick and tapering.

*Foliage.*—Medium green in color and medium heavy in texture, smooth and flat. The leaves have very finely serrated edges and the petioles have no spines. Stipules are medium to wide and terminate in pointed non-curling tips.

*Sepals.*—Five in number, heavy, rather short—1 to 1½ inches in length—branching only slightly, curling back tightly soon after buds begin to open, thereby usually exposing a pink color on many of the sepals.

*Blossoms.*—Large, often measuring 4½ to 5 inches across. Form very much like that of Frau Karl Druschki although having a somewhat fuller and less pointed center. Petals are notably incurving as the flower becomes two-thirds to fully opened; heavy petallage, numbering approximately 25 large and 25 smaller petals in the month of April in the latitude of Philadelphia.

The color effect of the blossom is flesh pink (Ridgway's Color Standards and Nomenclature, Plate XIII) in the central portion and the outer three to five rows of petals are white or slightly creamy with a slight suggestion of pink. This difference in color effect as between the center and the outer portions of the flower is mainly due to the fact that each petal is pink on the outer surface but white on its inner surface and as the outer rows of petals open and curl back the pink surface is hidden from view and the white revealed. There is, however, the further fact that the pink of the central petals is somewhat more intense than on the outer petals. At the base of each petal there is a slight yellow coloring.

The blossom is moderately fragrant.

The inverted cone or potential seed body, remaining after the petals are plucked away is notable and a prominently distinguishing character of this variety. Instead of the usual structure wherein the stamens and pistils rise from a level or slightly raised base only slightly above the plane of the attachment of the sepals, in this variety the relatively few stamens arise from this point but the numerous pistils are attached to the sides and top of a hard, pith-filled structure, rising approximately one-half inch above the point of sepal attachment. The pistils attached to this structure are of a reddish tint which gives the inverted cone-like structure a reddish tinted appearance.

This extraordinary central mass is a factor in causing the central grouping of petals to stand out prominently and remain solid until the flower begins to fade. It also apparently holds or locks the petals in position so that they do not drop off until they have fully withered and turned brown.

Having thus disclosed my invention, what I claim as new is:

The variety of hybrid tea rose herein shown and described, characterized particularly by its vigorous growth, free blooming habits, large, long lasting flowers having flesh-pink centers and white outer petals with touches of pink as described, and having a most unique raised cone-like structure in the central basal portion of each flower.

RUTH KAUCHER.